US008956858B2

(12) United States Patent
Dineen et al.

(10) Patent No.: US 8,956,858 B2
(45) Date of Patent: Feb. 17, 2015

(54) TACTICAL AND PORTABLE PCR/HRM GENOME IDENTIFICATION SYSTEM

(71) Applicant: SRC, Inc., North Syracuse, NY (US)

(72) Inventors: Zachary J Dineen, Syracuse, NY (US); David B. Knaebel, Manlius, NY (US)

(73) Assignee: SRC, Inc., North Syracuse, NY (US)

( * ) Notice: Subject to any disclaimer, the term of this patent is extended or adjusted under 35 U.S.C. 154(b) by 0 days.

(21) Appl. No.: 13/827,585

(22) Filed: Mar. 14, 2013

(65) Prior Publication Data

US 2014/0273185 A1    Sep. 18, 2014

(51) Int. Cl.
| | |
|---|---|
| C12M 1/00 | (2006.01) |
| C12M 3/00 | (2006.01) |
| C12M 1/34 | (2006.01) |
| C12M 1/36 | (2006.01) |
| C12M 1/38 | (2006.01) |
| C12Q 1/68 | (2006.01) |

(52) U.S. Cl.
CPC ..................................... C12Q 1/686 (2013.01)
USPC .................. 435/287.2; 435/283.1; 435/286.1; 435/287.1; 435/288.5

(58) Field of Classification Search
USPC ............................................. 435/283.1–309.4
See application file for complete search history.

(56) References Cited

U.S. PATENT DOCUMENTS

| | | | |
|---|---|---|---|
| 7,288,760 | B2 | 10/2007 | Weitz |
| 7,349,808 | B1 | 3/2008 | Kreiswirth |
| 7,710,269 | B2 | 5/2010 | Reep |
| 8,046,172 | B2 | 10/2011 | Kreiswirth |
| 2005/0118703 | A1 | 6/2005 | Su |
| 2006/0257853 | A1 | 11/2006 | Herman |
| 2007/0026426 | A1 | 2/2007 | Fuernkranz |
| 2008/0212643 | A1 | 9/2008 | McGahhey |
| 2009/0061489 | A1 | 3/2009 | Hanagata |
| 2010/0112565 | A1 | 5/2010 | Tobler |
| 2010/0136559 | A1 | 6/2010 | Okino |
| 2010/0240046 | A1 | 9/2010 | Palmer |
| 2011/0057117 | A1 | 3/2011 | Fawcett |
| 2011/0070587 | A1 | 3/2011 | Fuernkranz |
| 2011/0091877 | A1 | 4/2011 | Murphy |
| 2011/0105345 | A1 | 5/2011 | Cheng |
| 2011/0207137 | A1 | 8/2011 | Malik |
| 2012/0064523 | A1* | 3/2012 | Ecker et al. .................. 435/6.11 |

OTHER PUBLICATIONS

"Eco Real-Time PCR System." Illumina, Inc. [Online] Accessed Mar. 23, 2012. <www.ecoqper.com/products/ecoqper.ilmn>.

"LightCycler 480 System" Roche Applied Science. [Online] Accessed Mar. 23, 2012. <https://www.roche-applied-science.com/sis/rtpcr/htc/index.jsp?&id=htc_010000>.

(Continued)

*Primary Examiner* — Nathan Bowers
*Assistant Examiner* — Lydia Edwards
(74) *Attorney, Agent, or Firm* — George R. McGuire; Frederick J. M. Price; Bond Schoeneck & King, PLLC

(57) ABSTRACT

The present invention relates to a Polymerase Chain Reaction and High Resolution Melt genetic identification system, and, more specifically, to a tactical and portable Polymerase Chain Reaction and High Resolution Melt genetic analysis and identification system that is configured to determine and communicate analysis and identification results and a tiered confidence/alert level related to the analysis and identification results.

10 Claims, 3 Drawing Sheets

(56) References Cited

OTHER PUBLICATIONS

Figure 1:
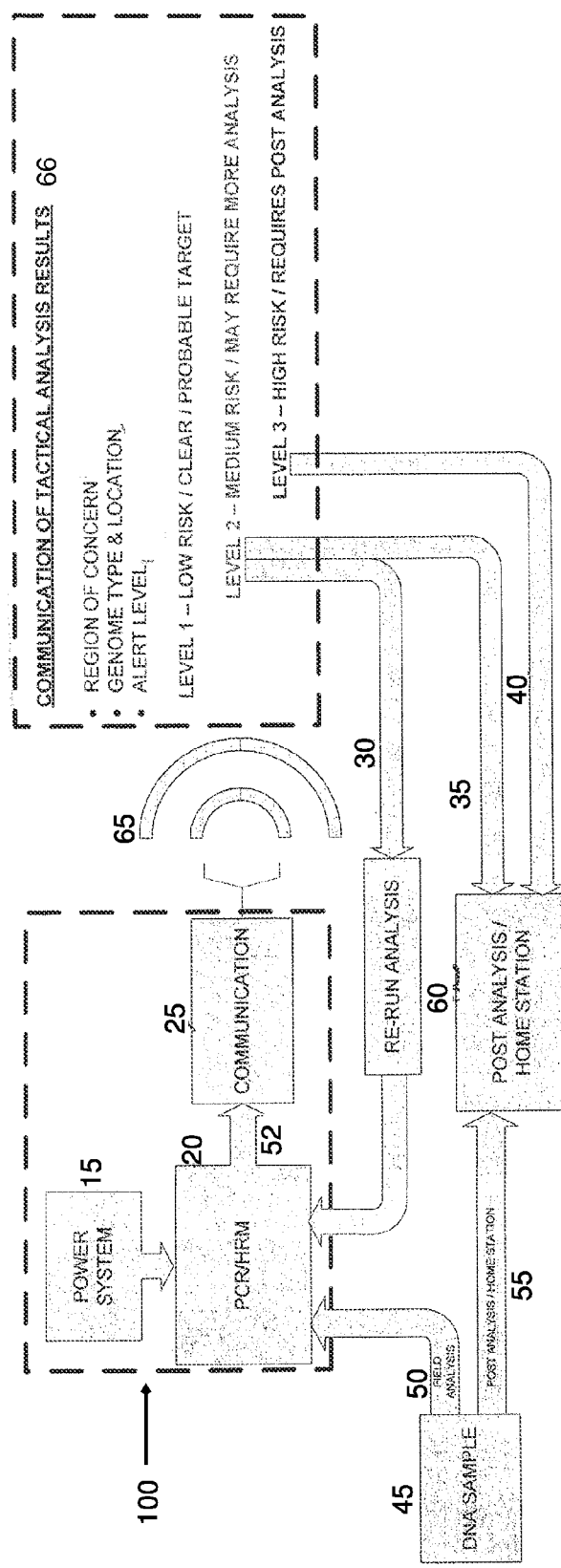

"Rotor-Gene Q" QIAGEN. [Online] Accessed Mar. 23, 2012. <www.qiagen.com/products/rotor-geneq.aspx#Tabs=t1>.

"BioMark HD System" Fluidigm. [Online] Accessed Mar. 23, 2012. <www.fluidigm.com/biomark-hd-system.html>.

"Thermal Cycler Dice Real Time System" Takara Bio, Inc. [Online] Accessed Mar. 22, 2012. <http://catalog.takara-bio.co.jp/en/PDFS/tp800.pdf>.

"ViiA 7 Real-Time PCR System" Life Technologies. [Online] Accessed Mar. 23, 2012. <www3.appliedbiosystems.com_cms_groups_mcb_marketing_documents_generaldocuments_cms_083988>.

* cited by examiner

TACTICAL AND PORTABLE PCR/HRM GENOME IDENTIFICATION SYSTEM

BACKGROUND OF THE INVENTION

1. Field of the Invention

The present invention relates to a Polymerase Chain Reaction and High Resolution Melt genetic identification system, and, more specifically, to a tactical and portable Polymerase Chain Reaction and High Resolution Melt genetic analysis and identification system that is configured to determine and communicate analysis and identification results and a tiered confidence/alert level related to the analysis and identification results.

2. Description of the Related Art

Polymerase Chain Reaction ("PCR") is a ubiquitous molecular biology tool used in thousands of different applications. In brief, this molecular biology tool is used to produce ("amplify") a sufficient number (sometimes millions to billions) of copies of a particular DNA sequence so that the sequence can adequately be used in these applications. Essentially, PCR makes a sample of DNA that is large enough so that the sample can be appropriately analyzed. As just one example of a typical application for PCR amplification, it is a common detection and/or identification method and tool used, for example, in clinical applications, scientific investigations, and in biological warfare agent ("BWA") detection systems.

High Resolution Melt ("HRM") is another molecular biology tool. This tool is used to detect a variety of differences (e.g., mutations, other types of genetic sequence differences) in samples of double stranded DNA, which is based on the detected melting temperature/behavior of the double stranded DNA sequence(s) at issue. HRM is performed post PCR amplification, which is performed to obtain a sufficient number of copies of the DNA sequence(s) of interest.

An end user would like the ability to perform genetic PCR and HRM genetic identity testing outside of the lab environment, i.e., in the field. This is a need because most commercially available PCR and PCR/HRM instruments are designed to be operated in a controlled and generally clean laboratory environment. In the field, however, it is expected that there will be wider temperature and humidity fluctuations, there may be no electrical supply, and other ambient environmental conditions may be outside the normal operating environment of these systems.

Accordingly, there is a continued need for a portable PCR/HMR genetic analysis and identification system.

BRIEF SUMMARY OF THE INVENTION

It is therefore a principal object and advantage of the present invention to provide a tactical and portable PCR and HMR genetic analysis and identification system that is configured to determine and communicate analysis and identification results and a tiered confidence/alert level related to the analysis and identification results.

Another object and advantage of the present invention is to provide a tactical and portable PCR and HMR genetic analysis and identification system that simple and is easy to use, is an all inclusive analysis, results, and reporting/communication system, provides accurate geo-location mapping, can run on most power devices including vehicle power, concealable, minimum size, weight, and power, has GPS capability, mechanically isolated for shock and vibration, easily transportable and deployable around the world (e.g., maximum 2 person carry and set-up), does not require a "technical" person to operate, and has a reliability and probability detection rating of up to 95.0%.

Another object and advantage of the present invention is to provide a tactical and portable PCR and HMR genetic analysis and identification system that is intended to be primarily portable and tactical in nature. This is accomplished, in part, by combining and modifying existing commercial-based technologies and combining them with custom hardware and software into a complete system.

In accordance with the foregoing objects and advantages, a tactical and portable PCR and HMR genetic analysis and identification system is provided comprising one or more of the following: a PCR/HRM module encompassed within a ruggedized enclosure, wherein the PCR/HRM module is structured and configured to perform PCR amplification and an HRM analysis on unknown DNA samples in the field; a computer processor encompassed within the ruggedized enclosure, interconnected to the PCR/HRM module, and programmed to compare the results of the PCR amplification and an HRM analysis on at least one unknown DNA sample by the PCR/HRM module to known control DNA samples, assign a probability of a match to one of the known control DNA samples, and to assign a confidence level to the DNA sample based on the probability of a match to the known control DNA; a communication module interconnected to the computer processor and configured to wirelessly transmit data from the computer processor and the PCR/HRM module to a computer device; wherein the computer processor is programmed to assign a confidence level as part of a tiered confidence level routine comprising a plurality of confidence levels, wherein a highest confidence level indicates a high probability of a match to one of the known control DNA samples and a lowest confidence level indicates a low probability of a match to one of the known control DNA samples.

Current commercial PCR/HRM systems are not designed to survive and operate in an environment outside of a controlled indoor laboratory environment. In addition, these machines are designed for standalone operation and have many features unnecessary for "field use" scenario, such as, LED's, push buttons, and the actual enclosures and packaging. These items can be removed and only the "critical to function" items can be used in the portable and tactical design, represented by the PCR/HRM module in FIG. 2, described below. "Field use" can be defined as outside of the normal laboratory environment and in a naturally occurring environment caused by terrestrial weather and an un-natural environment caused by dropping, road shock & vibration and any other human incident.

The details of one or more embodiments are described below and in the accompanying drawings. Other objects and advantages of the present invention will in part be obvious, and in part appear hereinafter.

BRIEF DESCRIPTION OF THE SEVERAL VIEWS OF THE DRAWING(S)

Figure 2:
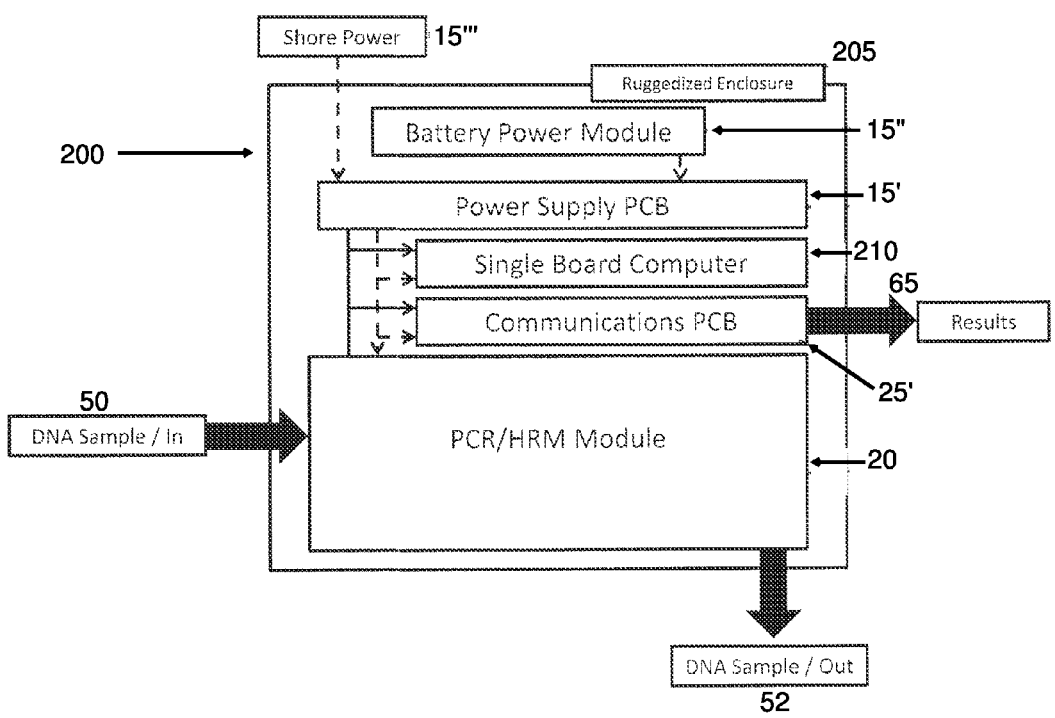
Figure 3:
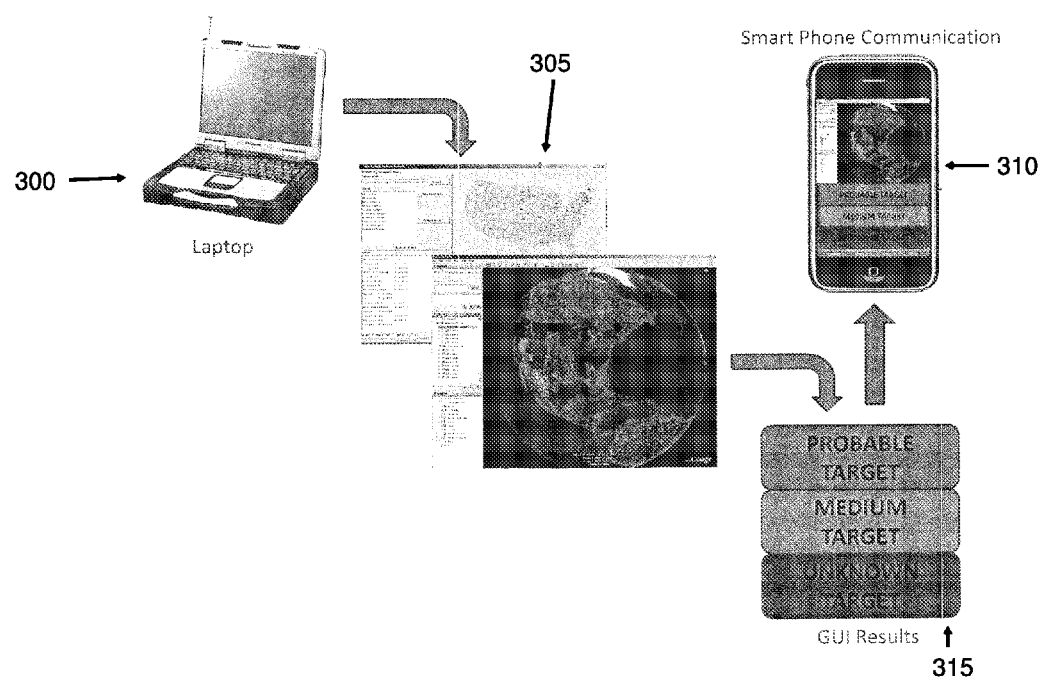

The present invention will be more fully understood and appreciated by reading the following Detailed Description in conjunction with the accompanying drawings, in which:

FIG. 1 is a schematic/flow chart representation of a tactical and portable PCR and HMR genetic analysis and identification system according to an embodiment of the present invention;

FIG. 2 is a schematic representation of a tactical and portable PCR and HMR genetic analysis and identification system 200, according to an embodiment of the present invention; and FIG. 3 is a schematic representation of results from a tactical and portable PCR and HMR genetic analysis and identification system being viewed and analyzed on various devices with GUIs, according to an embodiment of the present invention.

DETAILED DESCRIPTION OF THE INVENTION

Advantages of the invention are illustrated by the Examples set forth herein. However, the particular conditions and details are to be interpreted to apply broadly in the art and should not be construed to unduly restrict or limit the invention in any way.

As discussed further below, the tactical and portable PCR and HMR genetic analysis and identification system according to an embodiment of the present invention can include a PCR/HRM device, a power source, minimal liquid handling equipment, and kits for DNA extraction & purification and a well plate (e.g., a pre-made 96 well plate or 386 well plate). The plate can contain reagents necessary for PCR and HRM, where some plate wells are filled with reagents for the unknown DNA samples, and other wells contain control DNAs and reagents for comparison to the unknowns during the PCR/HRM run.

Once the sample or samples of concern are identified, a small portion is subjected to DNA extraction and purification using the commercial kits. The DNA is then distributed to a few wells the 96 well plate in a manner common for PCR. The plate, once filled with reagents, is placed into the PCR/HRM device.

The PCR/HRM device is turned on and a pre-determined PCR/HRM routine can be run on the device that subjects the sample to the PCR and subsequent HRM in a manner that is diagnostic for all known target samples. DNAs that are amplified during PCR and that have the appropriate HRM melt profiles in comparison to control DNAs are binned into three match groups: High probability of match to an known standard (>95%), moderate probability of a match to a known standard (>90; ≤94.9%), or low probability of a match to a known standard (<90.0%) Upon successful matching of the unknown DNA to a standard (here termed "genome identification"), the software of an embodiment of the present invention will provide the end-user with a tiered alert level. For example, a three (3) tier system could be established where a level of confidence or highest probability of a successful analysis and result would categorize a sample at a Level 1, 2 or 3, as set forth in Table 1 below.

TABLE 1

| Levels | Description |
|---|---|
| 1 | The end user is provided with a result identifying the sample as a probable match to a known DNA type and having a low risk of either a false negative or false positive. This response is one of clear and probable target, based on a greater than 95% similarity to standard target DNAs. A Level 1 result would provide the end-user with a specific genetic type and a regional mapping of the source's geographical location and/or point of origin via the software GUI. |
| 2 | The end user is provided with a result identifying the sample as a less close match to a known DNA and would be considered to have a medium risk of a false negative or false positive. The sample may require additional analysis. A Level 2 result would provide the end-user with, for example, a less confident assignment of geospatial origin (owing to perhaps a overlapping matches to several standard target DNA. This lack of certainty will also result in a more expansive regional mapping of the source material's geographical location and/or more likelihood for more than one point of origin via the software GUI. A Level 2 result could require additional tactical and portable PCR and HMR genetic analysis and identification system analysis, but would be most benefitted by further home station post analysis. |
| 3 | The end user is provided with a result identifying the sample as having a low probability of match to the target DNA standards, and therefore presents a high risk of a false positive or false negative, and the sample is not considered reliable for geolocation source assignments; the sample requires post analysis. A Level 3 result would require home station (not in-field) post analysis. |

Referring now to the drawings, wherein like reference numerals refer to like parts throughout, there is seen in FIG. 1 a schematic/flow chart representation of a tactical and portable PCR and HMR genetic analysis and identification system 10, according to an embodiment of the present invention. A power system 15, a PCR/HRM system 20, and a communication portion of the system 25 are shown. The communication portion 25 of the system can transmit results data wirelessly at 65. The wireless transmission can be accomplished through any wireless protocol/technology, including, but not limited to, ZigBee standards-based protocol, Bluetooth technology, and/or Wi-Fi technology. The wireless transmission can be over a network which can be any suitable wired or wireless network capable of transmitting communication, including but not limited to a telephone network, Internet, Intranet, local area network, Ethernet, online communication, offline communications, wireless communications and/or similar communications means. Further, this data can be encrypted as needed based on the sensitivity of the data, the location of the obtainment of the field sample, and or the identification of the collector, for example. Field DNA sample 45 is inputted at 50 (and outputted at 52 to the communication portion of the system 25) and can be analyzed in the field by the tactical and portable PCR and HMR genetic analysis and identification system 10 or remotely by the Post Analysis/Home Station 60.

As shown in the Communication of Tactical Analysis Results 66, if a Level 1 is indicated (low risk/clear/probable target), no further analysis of the field DNA sample 45 is required. If a Level 2 is indicated, (medium risk) more analysis of the field DNA sample 45 may be required. Arrow 30 shows follow-up analysis of the field DNA sample 45 by the tactical and portable PCR and HMR genetic analysis and identification system 100. Arrow 35 shows further analysis of the field DNA sample 45 by a remote PCR/HMR system 60. If a Level 3 is indicated, (high risk), post analysis of the field DNA sample 45 is required. Arrow 40 shows further analysis of the field DNA sample 45 by a remote PCR/HMR system 60.

As shown in FIG. 2, a tactical and portable PCR and HMR genetic analysis and identification system 200, according to an embodiment of the present invention is shown. The PCR/HRM module 20 can be designed and packaged in a ruggedized enclosure 205 (to protect from dropping, shaking, weather etc.) along with a battery power module 15", power supply PCB 15', single board computer 210 and a communications PCB 25'. The communication portion 25 of the system can transmit results data wirelessly at 65, and a DNA sample going in 50 and out 52 is also shown.

The ruggedized enclosure 205 can be custom designed to accommodate mounting and interconnection of the hardware items shown in FIG. 2. The material used for the design can be lightweight alloy or composite materials, such as aluminum or carbon fiber. These materials are known for excellent strength to weight ratio, their ability to dissipate heat efficiently and can be easily machined or formed into many different configurations.

The battery power module 15" is where DC batteries are placed to provide power to the system in a remote environment or away from shore power. The batteries supply power to the power supply PCB 15' that takes the incoming battery power or shore power and converts to useful power for the single board computer 210, communications PCB 25' and the PCR/HRM module 20.

The single board computer 210 provides the functionality to the system to control the PCR/HRM module 20, communications PCB 25' and to post-process the results of PCR/HRM DNA sample. Within the single board computer 210 is a bioforensics software module/tool/program code that enables classification and probability assignment results of the DNA samples. These classification and probability assignments can be filtered through a single board computer 210 database (the database can be internal or external where the computer 210 is wirelessly or in wired connection with the database (not shown)) in such a way as to provide confidence/alert level reporting (as discussed herein) to the user in a way that will report a high confidence of identification, a medium confidence of identification or a low confidence of identification. Those results are provided to the communications PCB 25'. The communications PCB 25' will take the results 315 and transfer that information to a host of computer devices e.g., desktop, laptop 300, smart phone 310, cell phone, computer tablet, and/or other portable computer like device where the results are displayed on an easy to read GUI 305 for an end user to assess and evaluate. See FIG. 3.

As will be appreciated by one skilled in the art, aspects of the present invention may be embodied as a system, method or computer program product. Accordingly, aspects of the present invention may take the form of an entirely hardware embodiment, an entirely software embodiment or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Although the present invention has been described in connection with a preferred embodiment, it should be understood that modifications, alterations, and additions can be made to the invention without departing from the scope of the invention as defined by the claims.

What is claimed is:

1. A tactical and portable PCR and HRM genetic analysis and identification system comprising:
    a PCR/HRM module encompassed within an enclosure, wherein said PCR/HRM module is structured and configured to perform PCR amplification and an HRM analysis on unknown DNA samples in the field;
    a computer readable medium having a bioforensics program code stored thereon and a computer processor encompassed within the enclosure, wherein said computer processor is interconnected to said PCR/HRM module, said computer processor is programmed by said bioforensics program to:
        compare the results of the PCR amplification and an HRM analysis on at least one unknown DNA sample by the PCR/HRM module to known control DNA samples,
        assign a probability of a match to one of the known control DNA samples, and
        assign a confidence level to the DNA sample based on the probability of a match to the known control DNA.

2. The system of claim 1, wherein said enclosure is made from materials selected from the group consisting of lightweight alloy and composite materials.

3. The system of claim 2, wherein the composite materials comprise aluminum or carbon fiber.

4. The system of claim 1, further comprising a communication module interconnected to said computer processor and configured to wirelessly transmit data from said computer processor and said PCR/HRM module to a computer device.

5. The system of claim 4, further comprising a battery power module interconnected to said PCR/HRM module, said computer processor, and said communication module.

6. The system of claim 5, further comprising a power supply PCB interconnected to said battery power module and configured to convert incoming battery power and convert the incoming battery power to power to be used by said PCR/HRM module, said computer processor, and said communication module.

7. The system of claim 4, wherein said computer processor is programmed by said bioforensics program to assign a confidence level as part of a tiered confidence level routine comprising a plurality of confidence levels, wherein a highest confidence level indicates a high probability of a match to one of the known control DNA samples and a lowest confidence level indicates a low probability of a match to one of the known control DNA samples.

8. The system of claim 7, wherein when the highest confidence level is assigned by said computer processor, said computer processor is further programmed by said bioforensics program to determine a specific genetic type of said previously unknown DNA sample.

9. The system of claim 7, wherein when the highest confidence level is assigned by said computer processor, said computer processor is further programmed by said bioforensics program to determine a regional mapping of the previously unknown DNA sample's geographic location or point of origin.

10. The system of claim 7, wherein when the lowest confidence level is assigned by said computer processor, said computer processor is further programmed by said bioforensics program to determine and indicate through the communication module that post-analysis of unknown DNA sample is required.

* * * * *